US00PP37528P2

(12) United States Plant Patent
Hansen

(10) Patent No.: US PP37,528 P2
(45) Date of Patent: Jul. 21, 2026

(54) ***HOSTA* PLANT NAMED 'Winning Ticket'**

(50) Latin Name: ***Hosta* hybrid**
Varietal Denomination: Winning Ticket

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,963

(22) Filed: Dec. 11, 2025

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

*Primary Examiner* — Susan Mccormick Ewoldt

(57) ABSTRACT

A new and distinct *Hosta* plant named 'Winning Ticket' with medium-sized, broadly-mounded habit of heavy-substance, flat, stiff, rounded, variegated foliage. Leaves have chartreuse-yellow margins, medium-green centers, with intermediate colors between. Flowers are near white with faint lavender blush on short scapes just above the foliage beginning in late June. The new plant is attractive for landscaping in the garden as a specimen, in mass and as a large container plant.

2 Drawing Sheets

Latin name and variety denomination of the plant: Botanical classification: *Hosta* hybrid.
Variety denomination: 'Winning Ticket'.

STATEMENT REGARDING PRIOR DISCLOSURES UNDER 37 CFR 1.77(B)(6)

*Hosta* 'Winning Ticket' was first introduced by the inventor as a non-enabling description through the International Cultivar Registration Authority registration in early 2025. No plants of *Hosta* 'Winning Ticket' have been sold, in this country or anywhere in the world, nor has any enabling disclosure of the new plant been made, more than one year prior the filing date of this application.

BACKGROUND AND ORIGIN OF THE PLANT

The present invention relates to a new and distinct *Hosta* plant, *Hosta* 'Winning Ticket' hereinafter also referred to as the new plant or by the cultivar name 'Winning Ticket'. *Hosta* 'Winning Ticket' is a cross between a proprietary unnamed streaked sport of 'Empress Wu' (U.S. Plant Pat. No. 20,774) and a selection from a cross between 'Mouse Tracks' (not patented) times 'Elatior' (not patented) known only by the breeder code H9-228 (not patented) at a wholesale perennial nursery in Zeeland, Michigan, USA in the summer of 2013. The new plant was assigned the code 13-270-1 and passed the initial evaluation in the summer of 2016. The new plant has been asexually propagated by division at the same nursery in Zeeland, Michigan, USA since 2019 and also by shoot-tip tissue culture with the resultant asexually propagated plants having retained all the same traits as the original plant in multiple generations. *Hosta* 'Winning Ticket' has been stable and reproduces true to type plants in successive generations of asexual reproduction.

BRIEF SUMMARY OF THE PLANT

There are over 7,000 *Hosta* cultivars established or registered by The American *Hosta* Society, which is the International Cultivar Registration Authority for the genus *Hosta*. The nearest comparison cultivars known to the inventor are: 'Cuyahoga' (not patented), 'Ice Cream' (not patented), 'Lakeside Circle O' (not patented), 'Mini Skirt' U.S. Plant Pat. No. 26,743, 'Rain Dancer' (not patented), and 'Tea and Crumpets' (not patented).

All of the above plants have a rounded variegated foliage with a green center and a yellowish variegated margins. 'Cuyahoga' has a slightly larger habit and the variegated margin is more creamy yellow. 'Ice Cream' has a smaller habit with smaller foliage and the flowers are slightly deeper lavender. 'Lakeside Circle O' has a smaller habit with smaller foliage and darker striped flowers. 'Mini Skirt' has a smaller habit with smaller foliage, the variegated margin becomes more creamy white, and the leaf blade is more cordate and less rounded with a coarse wave. 'Rain Dancer' has a much larger habit with larger foliage that is more glaucous, the scapes are taller. 'Tea and Crumpets' has a more upright and slightly smaller habit and smaller foliage, and the variegated margin is more creamy white. The leaf substance or thickness is thicker than all of the above comparison plants and the female parent.

The female parent has a larger habit and the leaves are variably streaked with variegation. The male parent has a smaller habit and the leaves are solid green.

Other *Hosta* cultivars may have similar colored variegated foliage, but 'Winning Ticket' is distinct from the above-listed *Hostas* and all other cultivars known to the inventor by the following combined traits:

1. Medium-sized, broadly-mounded plant habit with heavy-substance, flat, stiff, rounded, foliage;
2. Leaves are variegated with chartreuse-yellow margins and medium green centers, with intermediate colors between the margin and center;
3. Medium-sized flowers of near white with a faint lavender blush are on short scapes just over the foliage;
4. Very thick substance leaf blades.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color. The drawings show a five-year-old 'Winning Ticket' plant in a trial garden at a nursery in Zeeland, MI with supplemental fertilizer and water as needed.

DETAILED BOTANICAL DESCRIPTION

Figure 1:
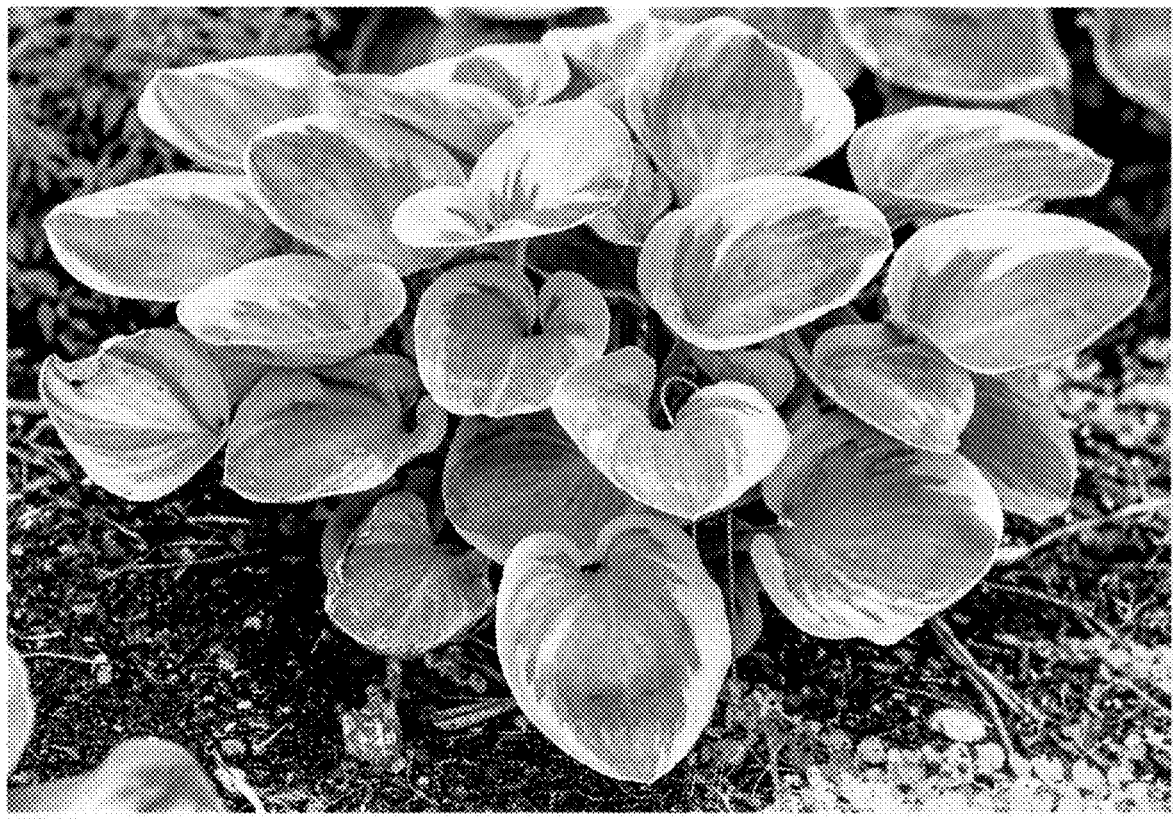
FIG. 1 shows the habit of a five-year-old plant.
Figure 2:
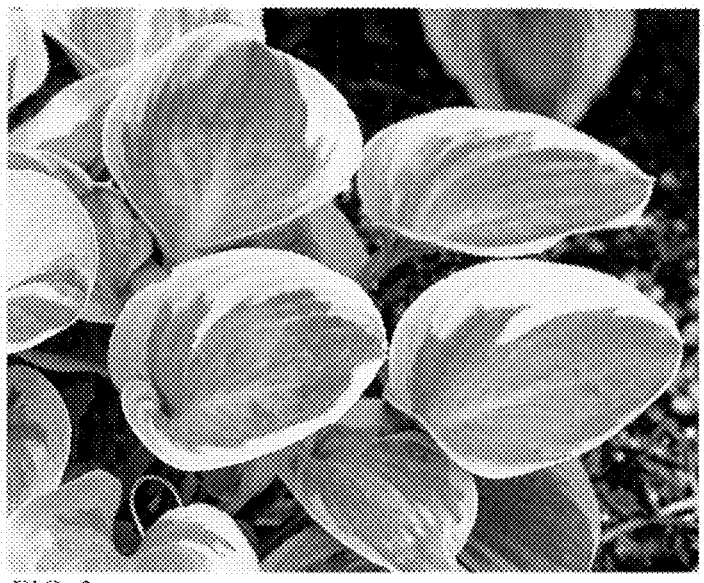
FIG. 2 shows a close-up of the foliage with variegation.
Figure 3:
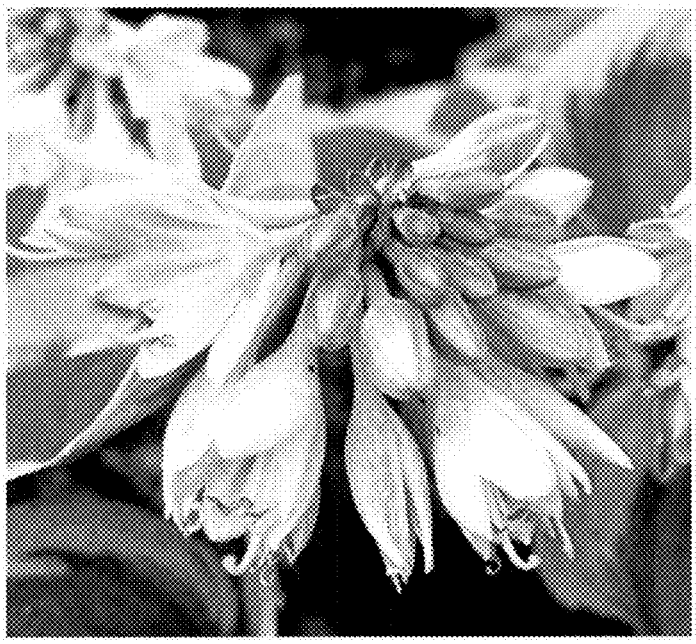
FIG. 3 shows a close-up of the flowers and buds.

The following descriptions and color references are based on the 2015 edition of The Royal Horticultural Society Colour Chart except where common dictionary terms are used. The new plant, *Hosta* 'Winning Ticket', has not been observed in all possible environments. The phenotype may vary slightly with different environmental conditions, such as temperature, light, fertility, moisture, and maturity levels, but without any change in the genotype. The following observations and size descriptions are of a five-year-old plant in a partially shaded trial garden in. Zeeland, Michigan with supplemental water and fertilizer.

Botanical classification: *Hosta* hybrid;

Parentage: The female or seed parent is a proprietary unnamed sport of 'Empress Wu', the male or pollen parent is H9-228;

Propagation: Garden division and sterile shoot-tip tissue culture;

Time to initiate roots from tissue culture: About two to three weeks;

Growth rate: Moderately vigorous to slow;

Crop time: About 12 to 14 weeks to finish during the summer in a one-liter container from rooted tissue culture plantlet;

Rooting habit: Normal, fleshy, lightly branching; color between RHS NN155A and RHS NN155B depending on soil content;

Plant shape and habit: Hardy herbaceous perennial with basal rosettes of leaves emerging from rhizomes producing a large, symmetrical, broad mound of leaves; about 8 divisions per plant with 4 flowering scapes; divisions to about 1.2 cm diameter at soil level;

Plant size: Foliage height about 31 cm above soil line to the top of the leaves and about 61 cm wide at the widest point about 10 cm above the soil line;

Foliage description: Ovate to rounded with maturity; broadly acute apex; cordate base; entire margin; glabrous and matte adaxial, and glabrous and slightly glaucous abaxial; blades mostly flat to slightly cupped near petiole;

Leaf blade size: To about 15.5 cm long, 13 cm wide at base; with yellowish margin of variable width between 2.5 cm and 3.8 cm wide;

Leaf blade color: Early season and expanding adaxial margin between RHS 144A and RHS 144B, adaxial center nearest RHS 137B, with intermediate colors between the margin and center comprising RHS 147C, and RHS 138D; early season and expanding abaxial margin between RHS 146D and RHS 148D, and center between RHS 138A and RHS 137C with intermediate colors comprising between RHS 148B and RHS 147B; mid-season and later summer adaxial margin more yellow than RHS 145A and lighter and more green than RHS 151A, center between RHS 137B and RHS 146A, intermediate region variable comprising RHS N148B, and RHS 144A, and between RHS 143A and RHS 144A; mid-season and later summer abaxial margin between RHS 160C and RHS 157A, center nearest RHS 138A, and between the margin and center intermediate colors comprising nearest RHS N138C, RHS 148C, RHS 146D, and between RHS N144A and RHS 144A;

Petiole: Glabrous; concavo-convex; stiff, strong and slightly flexible; mostly straight from base of plant to leaf base with little bending or arching; to about 20 cm long and 20 mm wide and 5 mm deep at base;

Petiole color: Adaxial and abaxial proximal 3 cm nearest RHS NN155B moderately maculate with dots smaller than 1 mm and between RHS N77B and RHS N79B, margin adaxial and abaxial about 1 mm wide between RHS 154D and RHS 160C, adaxial center between RHS 144A and RHS 138A, abaxial center between RHS 144A and RHS 138A, abaxial midrib nearest RHS 145C;

Veins: Parallel, moderately impressed adaxial, weakly bullate between veins; strongly costate abaxial side; about 10 to 12 pairs and one midrib;

Veins color: Adaxial margin portion nearest RHS 160D, center nearest RHS 147C; abaxial margin nearest RHS 160D, proximal midrib nearest RHS 145D, distal midrib and primary veins in center portion between RHS 146D and RHS 147C;

Flower description: Perfect; incomplete; single; actinomorphic; funnelform to campanulate; aspect outwardly to slightly upright; mostly secund; persist for normal period, usually one day on plant or as cut flower; about 28 flowers per scape;

Flower period: Scapes remain effective with flowering beginning early July for about three weeks in Michigan;

Flower bud: Clavate; with acute apex and fused tubular base; about 28 mm long in total, bulb portion about 17 mm long and 11 mm wide in bulb portion, tube about 11 mm long and 5 mm diameter;

Flower bud color: Nearest RHS NN155D in bulb with a faint blush of nearest RHS 86D, tube portion nearest RHS 157D;

Flower size: To about 36 mm long to exserted anthers; corolla to about 31 mm long and to about 29 mm across at apex; distal bell portion 22 mm long and tapering to corolla tube; corolla tube to about 10 mm long and 5 mm diameter near base;

Fragrance: None detected;

Tepals: Two sets of three; lanceolate with acute apex and fused base;

*Inner set*.—To about 33 mm long and 9 mm across slightly above fusion; fused in basal 17 mm and free in distal 16 mm.

*Inner set color*.—Adaxial blade three veins in distal blade portion nearest RHS NN155D toward the edges with the center nearer RHS 85D than RHS 85C, adaxial corolla tube nearest RHS NN155D; abaxial blade and corolla tube nearest RHS NN155D with a faint blush nearest RHS 85D.

*Outer set*.—To about 33 mm long and 10 mm across slightly above fusion; fused in basal 33 mm and free in distal 15 mm; translucent and vitreous along 1 mm wide margin.

*Outer set color*.—Adaxial blade three veins in distal blade portion nearest RHS NN155D toward the edges with the center nearer RHS 85D than RHS 85C, adaxial corolla tube nearest RHS NN155D; abaxial blade and corolla tube nearest RHS NN155D.

Gynoecium: Single; tri-carpelled; 26 mm long;

*Style*.—Single; cylindrical to slightly applanate; arcuate upward nearly 90° in distal 5 mm; about 20 mm long and 1 mm diameter; color distally nearest RHS NN155B and proximally nearest RHS 145D.

*Stigma*.—Flattened tri-lobed, micro-puberulent; about 1 mm across and 1 mm long; color nearest RHS 155D.

*Ovary*.—Superior; oblong ellipsoidal; acute apex and truncate base; longitudinally fluted; about 5 mm long and 3 mm diameter; color between RHS 146D and RHS 145A.

Androecium: Six;

*Filaments*.—Six; cylindrical; glabrous; arcuate upward about 90° in distal 5 mm portion; about 35 mm long and 1 mm diameter; color nearest RHS NN155B distally and in the proximal 2 mm nearest RHS 145D.

*Anthers*.—Oblong; dorsifixed; longitudinal; about 4 mm long, 2.2 mm across, and 1.5 mm thick; color adaxial nearest RHS 165B and abaxial nearest RHS 22C.

*Pollen*.—Abundant; smaller than 0.1 mm diameter; color nearest RHS 23A.

Pedicel: Cylindrical, glabrous, slightly glaucous; outwardly to slightly drooping; mostly secund; to about 8 mm long and 3 mm diameter;

Pedicel color: Nearest RHS 145C distally and nearest RHS 138A proximally;

Floral bracts: Subtending individual flowers; lanceolate; acute apex, truncate clasping base, margin entire; glabrous adaxial and abaxial; concavo-convex; tightly enclosing pedicel base; to about 15 mm long and naturally 6 mm across near base, flattening to about 13 mm across; decreasing in size distally; remaining after flower dries;

Bract color: Adaxial and abaxial margin between RHS 146D and RHS 145D, adaxial center 6 mm nearest RHS 148D and region between center and margin between RHS 138A and RHS 138B, abaxial center between RHS 146D and RHS 144B and region between center and margin between RHS 144A and RHS 143A;

Peduncle: Cylindrical; usually one per mature division and five per plant; moderately glaucous; glabrous; stiff, rigid; arching; to about 33 cm long and about 6 mm diameter at base; flowering in upper 8 cm with about 28 flowers per scape; flower spacing proximally to 1 cm and distally as close as 3 mm;

Peduncle color: Between RHS 138A and RHS 146C;

Fruit: Rare; three-valved dehiscent capsule; to about 17 cm long and 4 mm diameter; color as ripening nearest RHS 138B, at maturity nearest RHS 164C;

Seed: Elliptic; with flattened wing surrounding embryo positioned toward one end of ellipse; to about 7 mm long, 3 mm wide and 1 mm thick at embryo; typically, 12 to 30 per capsule; color between RHS 200A and RHS 202A with maturity;

Disease and pest tolerance and resistance: The new plant has not shown any resistance to pests, including *Odocoileus virginianus* and *Oryctotagus cuniculus*, and diseases common to *Hostas*.

Growth: The plant grows best and shows best coloration with plenty of moisture, adequate drainage and light shade, but is able to tolerate some drought when mature.

Hardiness: At least from USDA zone 3 through 9.

It is claimed:

1. A new and distinct ornamental *Hosta* plant named 'Winning Ticket' as herein described and illustrated.

* * * * *